United States Patent
Cheng et al.

(10) Patent No.: US 10,159,420 B2
(45) Date of Patent: Dec. 25, 2018

(54) NERVE IMPULSE SIGNAL STIMULATION DEVICE AND METHOD FOR FABRICATING THE SAME

(71) Applicant: National Chiao Tung University, Hsinchu (TW)

(72) Inventors: Yu-Ting Cheng, Hsinchu (TW); Chung-Yu Wu, Hsinchu (TW); Jui-Sheng Sun, Hsinchu (TW); Yu-Min Fu, Hsinchu (TW); Che-Yu Chen, Hsinchu (TW); Xin-Hong Qian, Hsinchu (TW)

(73) Assignee: National Chiao Tung University, Hsinchu (TW)

(*) Notice: Subject to any disclaimer, the term of this patent is extended or adjusted under 35 U.S.C. 154(b) by 195 days.

(21) Appl. No.: 15/217,348

(22) Filed: Jul. 22, 2016

(65) Prior Publication Data
US 2017/0245771 A1  Aug. 31, 2017

(30) Foreign Application Priority Data
Feb. 25, 2016  (TW) .............................. 105105632 A (51) Int. Cl.
*A61N 1/36* (2006.01)
*A61B 5/04* (2006.01)
(Continued)

(52) U.S. Cl.
CPC .......... *A61B 5/04001* (2013.01); *A61B 5/407* (2013.01); *A61B 5/6877* (2013.01);
(Continued)

(58) Field of Classification Search
CPC ......... A61B 5/04; A61B 5/407; A61B 5/6877; A61B 5/04001; A61N 1/36; A61N 1/05;
(Continued)

(56) References Cited

U.S. PATENT DOCUMENTS 5,078,674 A  1/1992  Cadwell
5,267,938 A  12/1993  Konotchick
(Continued)

OTHER PUBLICATIONS

Buzzi, et al., "A new handheld electromagnetic cortical stimulator for brain mapping during open skull neurosurgery: a feasibility study", 2015, pp. 3387-3390, IEEE, EMBC, Milan, Italy.
(Continued)

*Primary Examiner* — Catherine Voorhees
*Assistant Examiner* — Natasha Patel
(74) *Attorney, Agent, or Firm* — Mintz Levin Cohn Ferris Glovsky and Popeo, P.C.; Peter F. Corless; Steven M. Jensen (57) ABSTRACT

A nerve impulse signal stimulation device and a method for fabricating the same are provided. The nerve impulse signal stimulation device includes: a substrate having a first surface and a second surface opposite to the first surface; a first metal layer formed on the first surface of the substrate; a second metal layer formed on the first metal layer; a plurality of openings exposing a portion of the first surface of the substrate, a portion of the first metal layer and a portion of the second metal layer; and a ferromagnetic material attached to the second surface of the substrate. The openings cause the nerve impulse signal stimulation device to obtain a parallel circuit structure, thereby increasing the current load and the magnetic field intensity, reducing the size of the device, and ensuring the safety of operations.

12 Claims, 12 Drawing Sheets

(51) Int. Cl.
*A61B 5/00* (2006.01)
*A61N 2/00* (2006.01)
*A61N 1/05* (2006.01)

(52) U.S. Cl.
CPC ....... *A61N 1/0551* (2013.01); *A61N 1/36062* (2017.08); *A61N 2/006* (2013.01)

(58) Field of Classification Search
CPC ... A61N 1/36062; A61N 1/0551; A61N 2/006
See application file for complete search history.

(56) References Cited

U.S. PATENT DOCUMENTS

| | | | |
|---|---|---|---|
| 6,179,770 | B1 | 1/2001 | Mould |
| 2010/0016928 | A1* | 1/2010 | Zdeblick ................ A61N 1/05 607/72 |
| 2011/0042782 | A1* | 2/2011 | Chao ...................... H01L 28/10 257/531 |

OTHER PUBLICATIONS

Bonmassar, Giorgio, et al., "Microscopic magnetic stimulation of neural tissue", Nature Communications, 2012, pp. 1-10, MacMillan, USA.

Fu, Yu-Min et al., "A microfabricated coil for implantable applications of magnetic spinal cord stimulation", 2015, pp. 6912-6915, IEEE, EMBC, Milan, Italy.

Binkofski, Ferdinand, et al., "Stimulation of peripheral nerves using a novel magnetic coil", 1999, pp. 751-757, Muscle & Nerve, John Wiley & Sons, Inc., United States.

* cited by examiner

NERVE IMPULSE SIGNAL STIMULATION DEVICE AND METHOD FOR FABRICATING THE SAME

CROSS-REFERENCE TO RELATED APPLICATION

This application claims under 35 U.S.C. § 119(a) the benefit of Taiwanese Patent Application No. 105105632 filed Feb. 25, 2016, the entire contents of which are incorporated herein by reference.

BACKGROUND OF THE INVENTION

1. Field of the Invention

The present invention relates to nerve impulse signal stimulation devices and methods for fabricating the same, and, more particularly, to a nerve impulse signal stimulation devices applicable to spinal nerve-related operations and a method for fabricating the same.

2. Description of Related Art

During a spinal nerve-related operation, to prevent damage to a patient's spinal nerves, a stimulation device is usually placed on the spinal nerves to generate continuous nerve impulse signal stimulations. In the case that a doctor touches the spinal nerves, stimulation signals received by the spinal nerves will vary, which facilitates the doctor to determine whether the spinal nerves are damaged.

Nerve impulse signal stimulations can be divided into direct electric stimulations and magnetic stimulations. In a direct electric stimulation, wires are connected to two ends of the spinal nerves so as to directly apply an electric current to the spinal nerves. Variation of the electric current facilitates the doctor to determine whether the spinal nerves are damaged. However, it has been pointed out that nerve tissues may be damaged by a direct electric stimulation and a large impedance of the nerve tissues may adversely affect the electric stimulation effect.

In a magnetic stimulation, a magnetic field is generated by an electromagnet so as to induce an electric current in the spinal nerves. Different from the direct electric stimulation, the magnetic stimulation does not need to be in direct contact with the spinal nerves.

However, currently, magnetic stimulation devices are generally fabricated in a series manner, and consequently magnetic fields generated by these devices are limited by electric current loads that wires can withstand. To increase the magnetic field of a magnetic stimulation device, input current needs to be increased. For example, a common copper wire can withstand an electric current density of 1 mA/μm², and an electric current having a density greater than 1 mA/μm² easily causes the copper wire to be burned.

Further, the magnetic stimulation device must be placed in a space under the spine to induce an electric current in the spinal nerves. However, limited by the space, to increase the magnetic field of the magnetic stimulation device, the number of windings of the wire needs to be increased, thus increasing the volume of the magnetic stimulation device.

Therefore, how to overcome the above-described drawbacks has become critical.

SUMMARY OF THE INVENTION

In view of the above-described drawbacks, the present invention provides a method for fabricating a nerve impulse signal stimulation device, which comprises: providing a substrate having a first surface and a second surface opposite to the first surface; forming a first metal layer on the first surface of the substrate; forming a second metal layer on the first metal layer; forming on the second metal layer a patterned resist layer that covers the second metal under the patterned resist layer; continuing formation of the second metal layer on a portions of the second metal layer that is not covered by the patterned resist layer; removing the patterned resist layer and the first metal layer and the second metal layer that are under the patterned resist layer so as to form a plurality of openings that expose a portion of the first surface of the substrate, a portion of the first metal layer and a portion of the second metal layer; and attaching a ferromagnetic material to the second surface of the substrate.

The present invention further provides a nerve impulse signal stimulation device, which comprises: a substrate having a first surface and a second surface opposite to the first surface; a first metal layer formed on the first surface of the substrate; a second metal layer formed on the first metal layer; a plurality of openings exposing a portion of the first surface of the substrate, a portion of the first metal layer and a portion of the second metal layer; and a ferromagnetic material attached to the second surface of the substrate.

In an embodiment, each of the openings has a rib shape, and the openings are arranged in parallel to one another.

In an embodiment, the first metal layer is made of titanium.

In an embodiment, the second metal layer is made of copper.

In an embodiment, the nerve impulse signal stimulation device further comprises a third metal layer formed on side surfaces of the first metal layer and upper and side surfaces of the second metal layer, and a fourth metal layer formed on upper and side surfaces of the third metal layer.

In an embodiment, the ferromagnetic material is made of cobalt, iron, bismanol, nickel, manganese antimonide, chromium oxide, manganese arsenide or manganese-zinc alloy.

According to the present invention, a plurality of openings are formed to cause the nerve impulse signal stimulation device to obtain a parallel circuit structure, thereby increasing the current load and the magnetic field intensity, reducing the size of the device, and ensuring the safety of operations.

DETAILED DESCRIPTION OF PREFERRED EMBODIMENTS

The following illustrative embodiments are provided to illustrate the disclosure of the present invention, these and other advantages and effects can be apparent to those in the art after reading this specification.

It should be noted that all the drawings are not intended to limit the present invention. Various modifications and variations can be made without departing from the spirit of the present invention. Further, terms such as "first", "second", "on", "a" etc. are merely for illustrative purposes and should not be construed to limit the scope of the present invention.

FIGS. 1A to 1G are schematic diagrams showing a method for fabricating a nerve impulse signal stimulation device 1 according to the present invention.

Figure 1A:
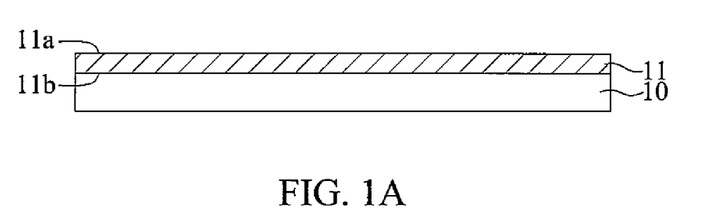
FIGS. 1A to 1G are schematic diagrams showing a method for fabricating a nerve impulse signal stimulation device according to the present invention.

Referring to FIG. 1A, a substrate 11 having a first surface 11a and a second surface 11b opposite to the first surface 11a is provided, and a carrier layer 10 is attached to the second surface 11b of the substrate 11.

The carrier layer 10 can be made of silicon, and the substrate 11 can be made of a polyimide film such as Kapton.

Figure 1B:
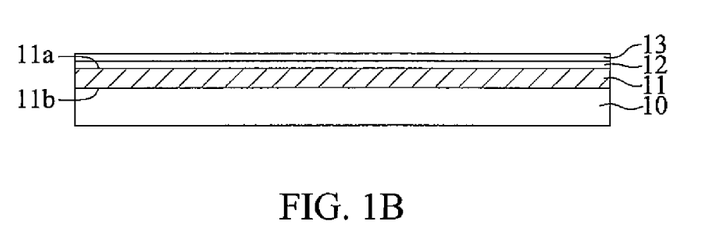

Referring to FIG. 1B, a first metal layer 12 is formed on the first surface 11a of the substrate 11, and then a second metal layer 13 is formed on the first metal layer 12.

The first metal layer 12 can be made of titanium, and the second metal layer 13 can be made of copper. Both the first metal layer 12 and the second metal layer 13 can be formed by sputtering.

Figure 1C:
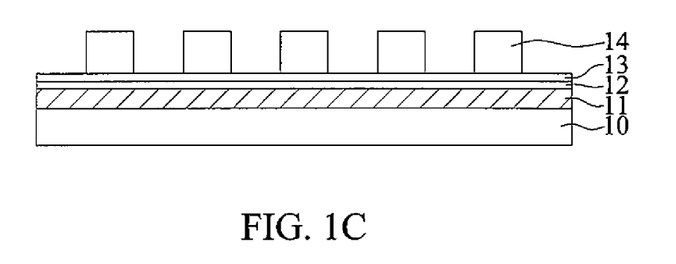

Referring to FIG. 1C, a patterned resist layer 14 is formed on the second metal layer 13. The patterned resist layer 14 can be formed through a lithography process that includes, but not limited to, dehydration bake, spin coating, soft bake, exposure, development, hard bake and so on.

Figure 1D:
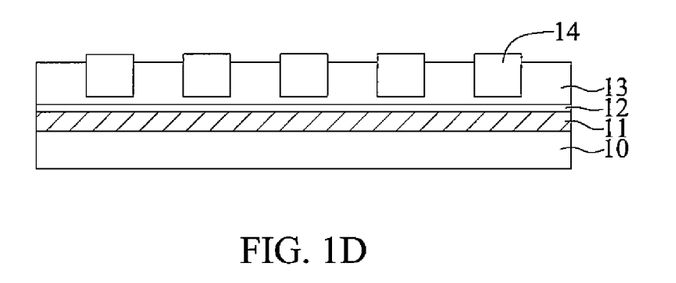

Referring to FIG. 1D, formation of the second metal layer 13 is continued on a portion of the second metal layer 13 that is not covered by the patterned resist layer 14. In an embodiment, the second metal layer 13 can be formed by electroplating.

Figure 1E:
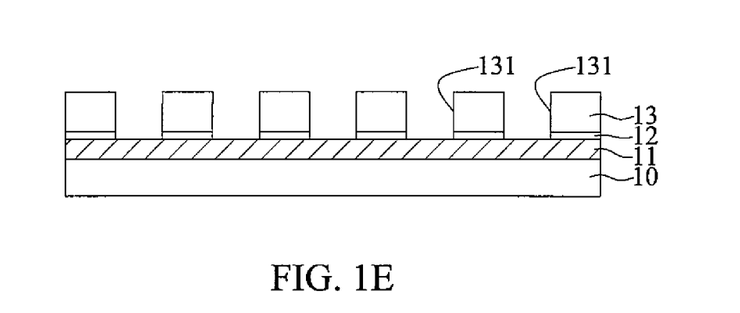

Referring to FIG. 1E, the patterned resist layer 14 and the first metal layer 12 and the second metal layer 13 that are under the patterned resist layer 14 are removed so as to form a plurality of openings 131 that expose a portion of the first surface 11a of the substrate 11, a portion of the first metal layer 12 and a portion of the second metal layer 13.

The patterned resist layer 14 can be removed by acetone, the second metal layer 13 under the patterned resist layer 14 can be removed by a copper etching solution, and the first metal layer 12 under the second metal layer 13 can be removed by hydrofluoric acid.

In an embodiment, after the patterned resist layer 14 and the first metal layer 12 and the second metal layer 13 that are under the patterned resist layer 14 are removed, a third metal layer made of such as nickel (not shown) is formed on side surfaces of the first metal layer 12 and upper and side surfaces of the second metal layer 13 by electroless plating so as to encapsulate the first metal layer 12 and the second metal layer 13, and a fourth metal layer made of such as gold (not shown) is formed on upper and side surfaces of the third metal layer to encapsulate the third metal layer, thereby preventing oxidation of the second metal layer 13 and achieving a better biocompatibility.

Figure 1F:
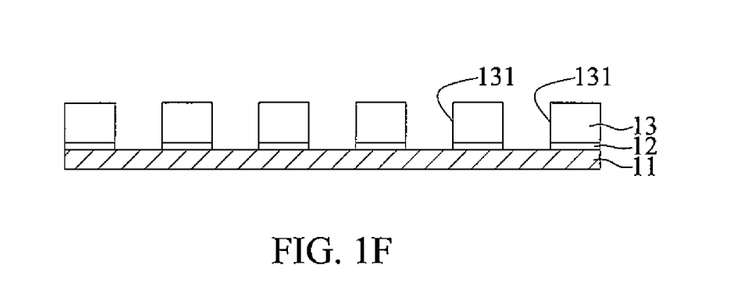

Referring to FIG. 1F, the carrier layer 10 is removed.

Figure 1G:
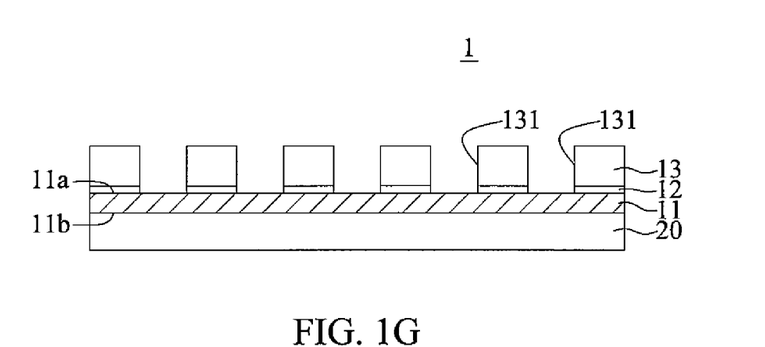

Referring to FIG. 1G, a ferromagnetic material 20 is attached to the second surface 11b of the substrate 11 so as to form the nerve impulse signal stimulation device 1.

The ferromagnetic material 20 can be made of cobalt, iron, bismanol, nickel, manganese antimonide, chromium oxide, manganese arsenide or manganese-zinc alloy and so on.

Figure 2A:
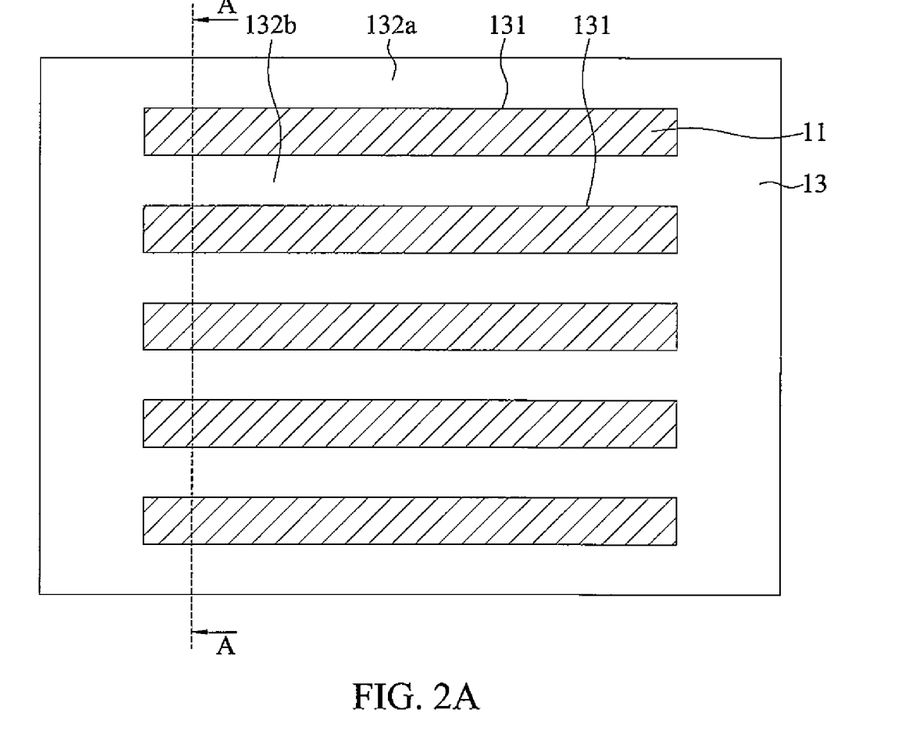
FIG. 2A is a schematic diagram of a parallel structure of the nerve impulse signal stimulation device according to an embodiment of the present invention.

FIG. 2A is a schematic diagram of a parallel structure of the nerve impulse signal stimulation device according to an embodiment of the present invention. Referring to FIG. 2A, the second metal layer 13 is formed on the substrate 11, and the openings 131 expose a portion of the first surface 11a of the substrate 11, a portion of the first metal layer 12 and a portion of the second metal layer 13. Each of the openings 131 has a rib shape, the openings 131 are arranged in parallel to one another, and the second metal layer 13 is divided by the openings 131 into a plurality of strip-shaped structures 132a, 132b. The strip-shaped structures 132a, 132b are equivalent to a parallel circuit so as to allow the second metal layer 13 to have a parallel circuit configuration.

Figure 2B:
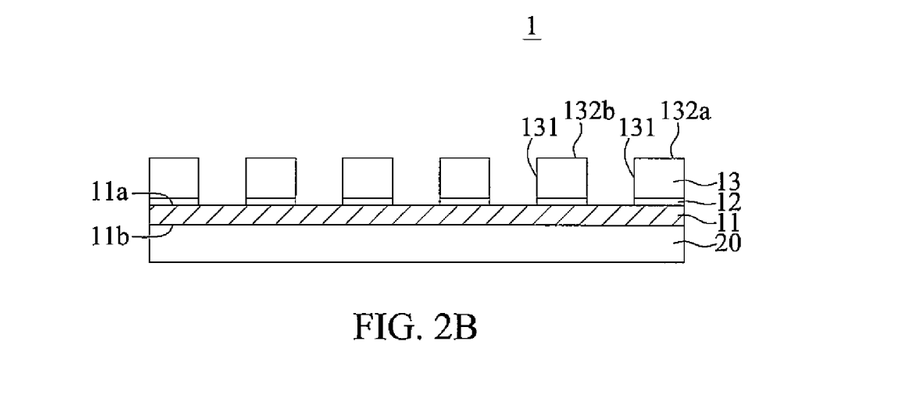
FIG. 2B is a structural cross-sectional view of the nerve impulse signal stimulation device according to an embodiment of the present invention.

FIG. 2B is a structural cross-sectional view of the nerve impulse signal stimulation device 1 taken along a line A-A of FIG. 2A. Referring to FIG. 2B, the second surface 11b of the substrate 11 is attached to the ferromagnetic material 20, thus forming the nerve impulse signal stimulation device 1.

Figure 3A:
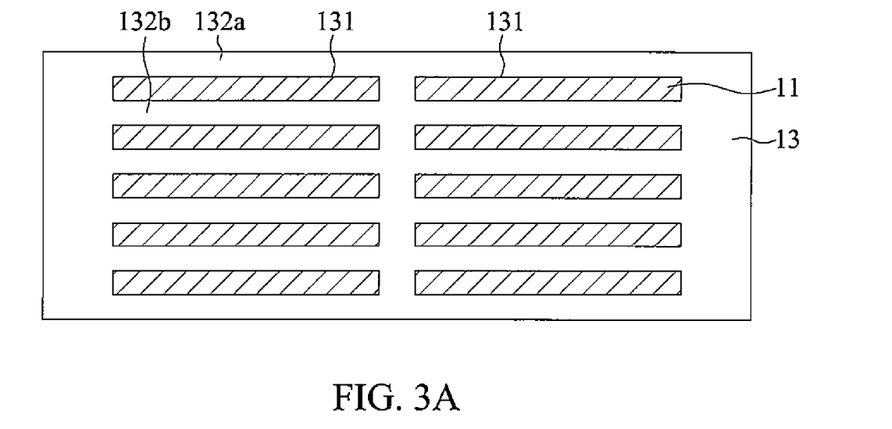
FIG. 3A is a schematic diagram of a parallel structure of the nerve impulse signal stimulation device according to another embodiment of the present invention.

FIG. 3A is a schematic diagram of a parallel structure of the nerve impulse signal stimulation device according to another embodiment of the present invention. FIG. 3A differs from FIG. 2A in that the openings 131 are arranged in two or more columns so as to increase the number of the parallel circuit.

Figure 3B:
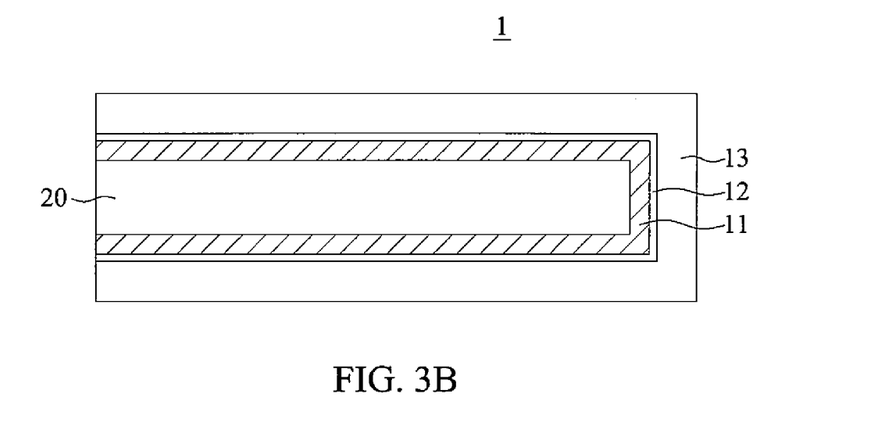
FIG. 3B is a structural side view of the nerve impulse signal stimulation device according to another embodiment of the present invention.

FIG. 3B is a structural side view of the nerve impulse signal stimulation device 1 according to another embodiment of the present invention. Referring to FIG. 3B, similar to FIG. 2B, the second surface 11b of the substrate 11 is attached to the ferromagnetic material 20 to encapsulate both upper and lower surfaces of the ferromagnetic material 20, thus forming the nerve impulse signal stimulation device 1.

Figure 4A:
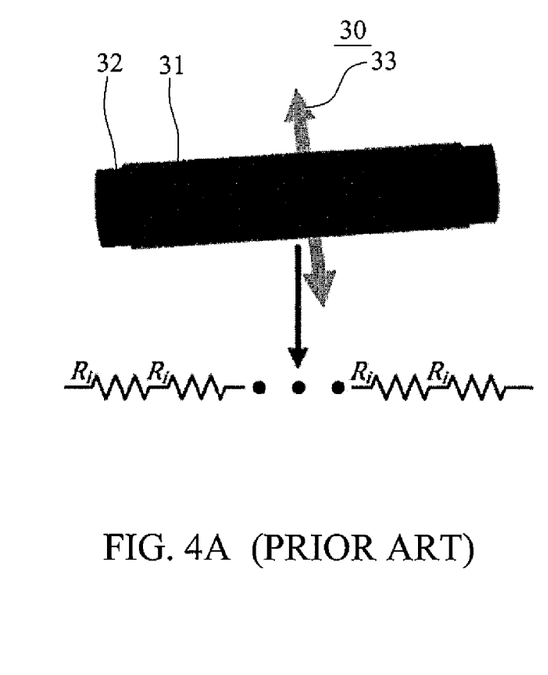
FIG. 4A is a schematic diagram of a conventional stimulation device.
Figure 4B:
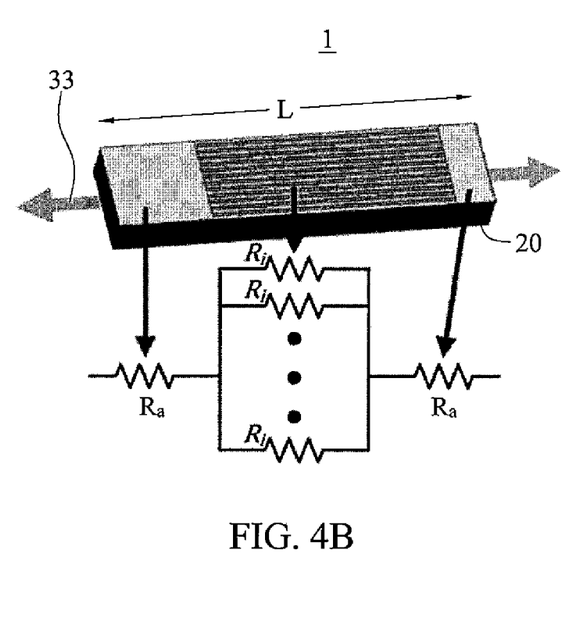
FIG. 4B is a schematic diagram of a nerve impulse signal stimulation device according to the present invention.

FIG. 4A is a schematic diagram of a conventional stimulation device 30, and FIG. 4B is a schematic diagram of the nerve impulse signal stimulation device 1 according to the present invention.

Referring to FIG. 4A, the conventional stimulation device 30 has a wire 31 wound around a core 32 and a total resistance $R_{total}$ equivalent to a series circuit as shown at a lower portion of FIG. 4A. Therein, the number of windings of the wire 31 is N, and each of the windings has a resistance value of $R_i$. Thus, the total resistance $R_{total}$ of the conventional stimulation device 30 is represented as:

$$R_{total} = \sum_{i=1}^{N} R_i = NR_i$$

The power P of the conventional stimulation device 30 is represented as:

$$P = I^2(NR_i)$$

Particularly, due to the direction of the magnetic field generated by the conventional stimulation device 30, the direction 33 of spinal nerves must be identical to the winding direction of the wire 31 so as to cause the conventional stimulation device 30 to generate a maximum induced current in the spinal nerves.

Referring to FIG. 4B, the total resistance $R_{total}$ of the nerve impulse signal stimulation device 1 according to the present invention is equivalent to a parallel circuit as shown at a lower portion of FIG. 4B. Therein, the parallel circuit has N resistors $R_i$ (resistors $R_a$ of FIG. 4B have very small values and are negligible). Thus, the total resistance $R_{total}$ of the nerve impulse signal stimulation device 1 is represented as:

$$R_{total} = \left(\sum_{i=1}^{N} \frac{1}{R_i}\right)^{-1} = \frac{R_i}{N}$$

The power P of the nerve impulse signal stimulation device 1 is represented as:

$$P = (NI)^2 \left(\frac{R_i}{N}\right) = I^2 NR_i$$

Particularly, the length direction L of the nerve impulse signal stimulation device 1 is identical to the direction 33 of spinal nerves so as to generate a maximum induced current in the spinal nerves.

Therefore, the nerve impulse signal stimulation device 1 according to the present invention consumes the same power P as the conventional stimulation device 30.

Figure 5A:
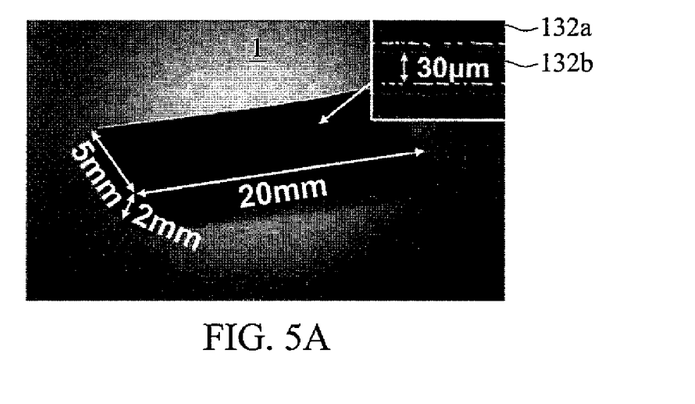
FIG. 5A shows a practical example of a nerve impulse signal stimulation device according to the present invention.

FIG. 5A shows a practical example of the nerve impulse signal stimulation device 1 according to the present invention.

Referring to FIG. 5A in combination with FIGS. 1A to 1G, the nerve impulse signal stimulation device 1 is fabricated through the following steps:

(a) attaching a substrate 11 made of a polyimide film (such as Kapton®, Krempel, Germany) and having a thickness of 75 μm to a carrier layer 10;

(b) sputtering titanium having a thickness of 30 nm on the substrate 11 so as to form a first metal layer 12;

(c) sputtering copper having a thickness of 120 nm on the first metal layer 12 so as to form a second metal layer 13;

(d) forming a patterned resist layer 14 (such as AZ-4620, Microchemicals) on the second metal layer 13 to cover the second metal layer under the patterned resist layer;

(e) continuing to deposit copper having a thickness of 4 μm on a portion of the second metal layer 13 that is not covered the patterned resist layer 14 so as to increase the thickness of the second metal layer 13;

(f) removing the patterned resist layer 14 by acetone;

(g) etching or removing the first metal layer 12 and the second metal layer 13 that are under the patterned resist layer 14 by hydrofluoric acid and a copper etching solution, respectively, so as to form a plurality of openings 131 (as shown in FIG. 2A), wherein 125 strip-shaped structures 132a, 132b are formed (that is, 125 strips in parallel) and each of the strip-shaped structures 132a, 132b has a width of 30 μm;

(h) plating or forming a third metal layer made of nickel, for example, on side surfaces of the first metal layer 12 and upper and side surfaces of the second metal layer 13 by electroless plating, plating or forming a fourth metal layer made of gold, for example, on upper and side surfaces of the third metal layer, and then removing the carrier layer 10; and (i) attaching a ferromagnetic material 20 to a second surface 11b of the substrate 11 so as to form the nerve impulse signal stimulation device 1, wherein the ferromagnetic material 20 is made of manganese-zinc alloy and has a size of 20 mm in length, 5 mm in width and 2 mm in height.

Figure 5B:
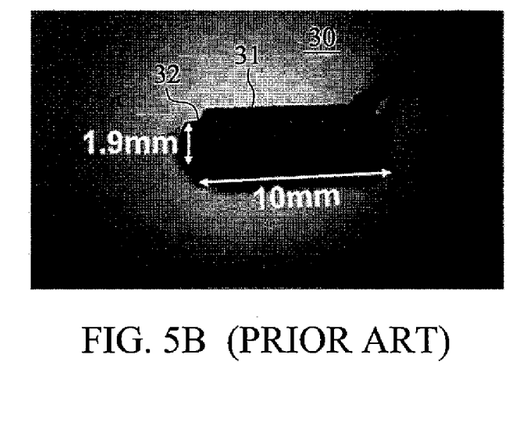
FIG. 5B shows a practical example of a conventional stimulation device.

FIG. 5B shows a practical example of the conventional stimulation device 30. Referring to FIG. 5B, the conventional stimulation device 30 is provided by Ainhsin electronic Co., Ltd. The conventional stimulation device 30 has a core 32 and a wire 31 having 50 windings. The wire 31 is made of copper and has a diameter of 0.3 mm, and the core 32 has a diameter of 1.9 mm and a length of 10 mm.

The conventional stimulation device 30 can withstand an input current of about 200 mA. If the input current is above 200 mA, the wire 31 will be burned.

Figure 6A:
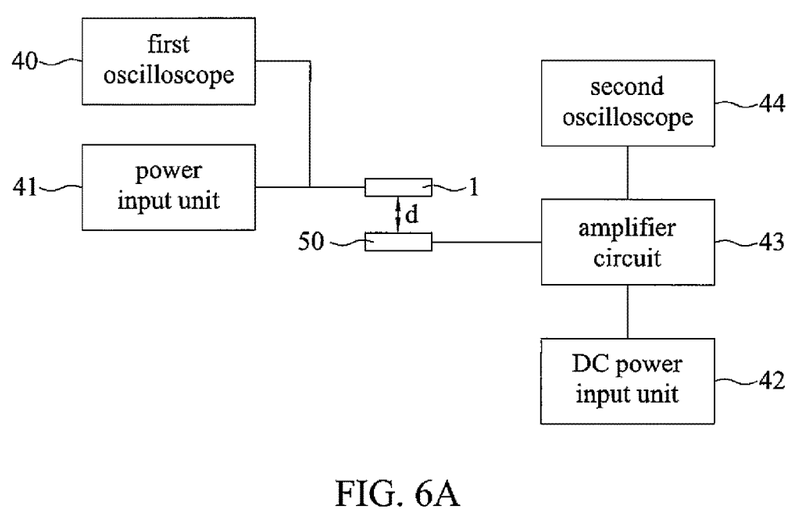
FIG. 6A is a schematic diagram of an apparatus for testing the nerve impulse signal stimulation device according to the present invention.
Figure 6B:
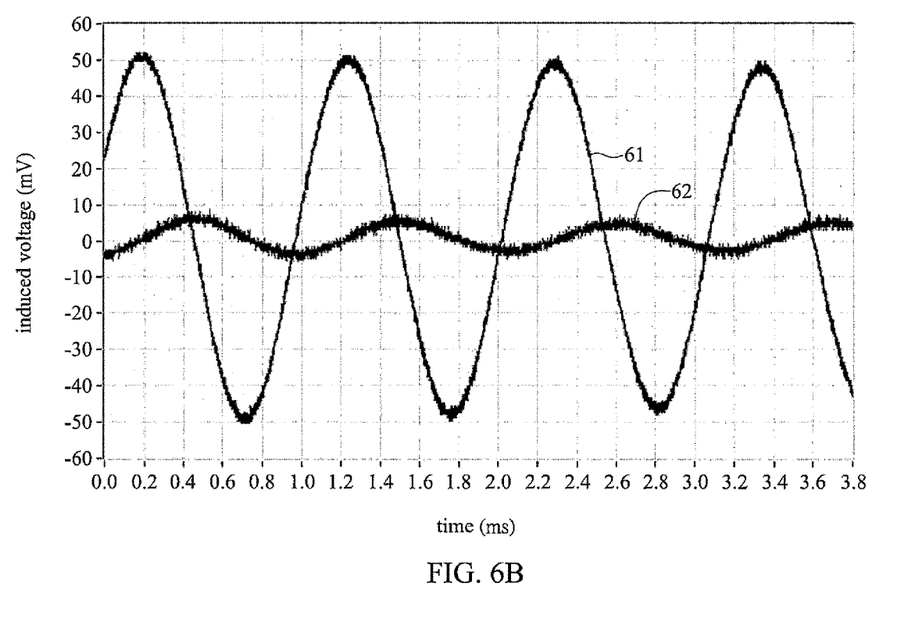
FIG. 6B is a plot diagram of test signals of the nerve impulse signal stimulation device according to the present invention.

FIG. 6A is a schematic diagram of an apparatus for testing the nerve impulse signal stimulation device 1 according to the present invention, and FIG. 6B is a plot diagram of test signals of the nerve impulse signal stimulation device according to the present invention.

Referring to FIG. 6A, the nerve impulse signal stimulation device 1 according to the present invention is connected to a first oscilloscope 40 and a power input unit 41. The power input unit 41 is used to provide power required by the nerve impulse signal stimulation device 1, and the first oscilloscope 40 is used to detect whether the power inputted by the power input unit 41 into the nerve impulse signal stimulation device 1 is correct.

The nerve impulse signal stimulation device 1 can be replaced by the conventional stimulation device 30 for cross comparison.

A test wire 50 is connected to an amplifier circuit 43, and a DC power input unit 42 is used to provide power to the amplifier circuit 43. The nerve impulse signal stimulation device 1 is separated from the test wire 50 by a distance d. An electric current signal obtained by the test wire 50 is displayed in a second oscilloscope 44.

Referring to FIG. 6B, when an electric current of 1.5 A and a square wave of 1 kHz are input to test the nerve impulse signal stimulation device 1 that is moved close to the test wire 50, the second oscilloscope 44 (as shown in FIG. 6A) displays a waveform 61 with a peak value up to 50 mV. When the nerve impulse signal stimulation device 1 is moved away from the test wire 50, the second oscilloscope 44 displays a waveform 62.

The nerve impulse signal stimulation device 1 generates an electric current in the test wire 50. For ease of illustration, the electric current is converted into a voltage, as shown in FIGS. 6B, 7C, 7D and 8.

Figure 7A:
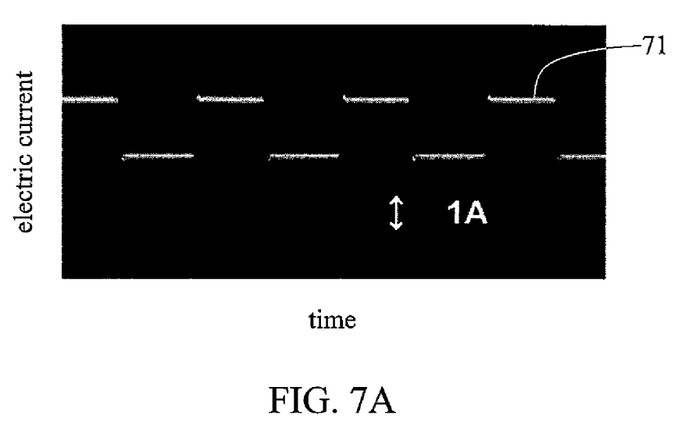
FIG. 7A is a diagram of an input waveform of the nerve impulse signal stimulation device according to the present invention.
Figure 7B:
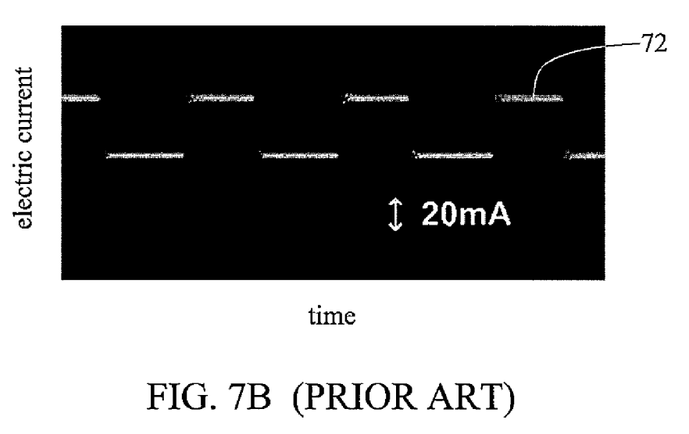
FIG. 7B is a diagram of an input waveform of the conventional stimulation device.
Figure 7C:
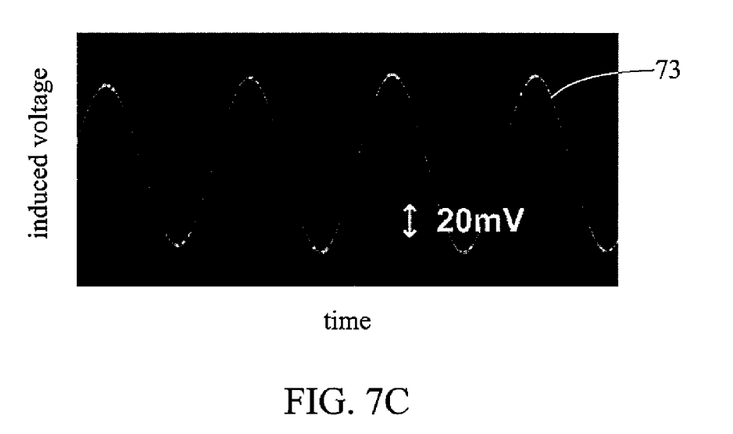
FIG. 7C is a plot diagram of voltage induced by the nerve impulse signal stimulation device according to the present invention.
Figure 7D:
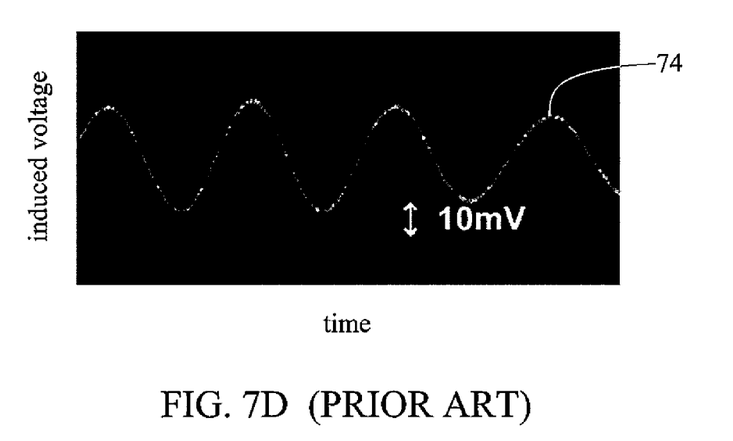
FIG. 7D is a plot diagram of voltage induced by the conventional stimulation device.

FIG. 7A is a diagram of an input waveform of the nerve impulse signal stimulation device according to the present invention, FIG. 7B is a diagram of an input waveform of the conventional stimulation device, FIG. 7C is a plot diagram of voltage induced by the nerve impulse signal stimulation device according to the present invention, and FIG. 7D is a plot diagram of voltage induced by the conventional stimulation device.

Referring to FIGS. 7A and 7B, the power input unit 41 (as shown in FIG. 6A) inputs an electric current of 1.5 A to the nerve impulse signal stimulation device 1 to present a curve 71, and the power input unit 41 (as shown in FIG. 6A) inputs an electric current of 30 mA to the conventional stimulation device 30 to present a curve 72. In FIGS. 7A and 7B, the longitudinal axis represents electric current, and the horizontal axis represents time.

An electric current of 30 mA is input to the conventional stimulation device 30, and the number of the windings of the conventional stimulation device 30 is 50 (as described above with regard to FIG. 5B). According to the equation B=μni, the conventional stimulation device 30 generates a magnetic field that is equivalent to a conventional stimulation device 30 having an input current of 1.5 A and a winding number of one.

Referring to FIGS. 7C and 7D, when the nerve impulse signal stimulation device 1 according to the present invention is separated from the test wire 50 by a distance d of 1 mm, a waveform 73 is generated; and when the conventional stimulation device 30 is separated from the test wire 50 by a distance d of 1 mm, a waveform 74 is generated. In FIGS. 7C and 7D, the longitudinal axis represents induced voltage, and the horizontal axis represents time.

Therefore, under the same test condition, an induced voltage (see a curve 73) generated by the nerve impulse signal stimulation device 1 according to the present invention is greater than an induced voltage (see a curve 74) generated by the conventional stimulation device 30.

Figure 8:
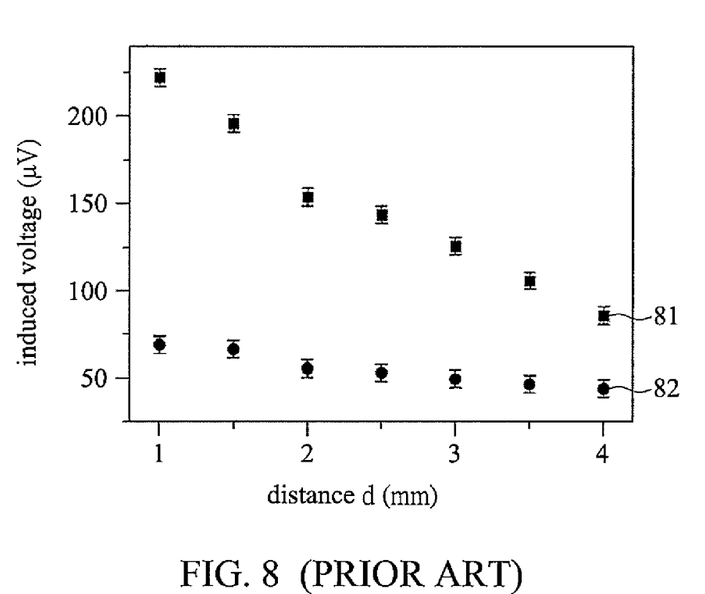
FIG. 8 is a plot diagram showing a relationship between distance and voltage induced by the nerve impulse signal stimulation device according to the present invention and the conventional stimulation device.

FIG. 8 is a plot diagram showing a relationship between a distance and a voltage induced by the nerve impulse signal stimulation device according to the present invention and the conventional stimulation device. Referring to FIG. 8, the horizontal axis represents a distance d between the nerve impulse signal stimulation device 1 or the conventional stimulation device 30 and the test wire 50, and the longitudinal axis represents a voltage that is induced by the nerve impulse signal stimulation device 1 or the conventional stimulation device 30 and the induced voltage is not amplified by the amplifier circuit 43. The voltage induced by the nerve impulse signal stimulation device 1 is denoted by 81 and the voltage induced by the conventional stimulation device 30 is denoted by 82. An electric current of 1.5 A is input to the nerve impulse signal stimulation device 1, and an electric current of 30 mA is input to the conventional stimulation device 30.

Referring to FIG. 8, the voltage induced by the nerve impulse signal stimulation device 1 in the test wire 50 is greater than the voltage induced by the conventional stimulation device 30 in the test wire 50, no matter what the distance d is. Therefore, the nerve impulse signal stimulation device 1 according to the present invention has a better induction effect.

Figure 9:
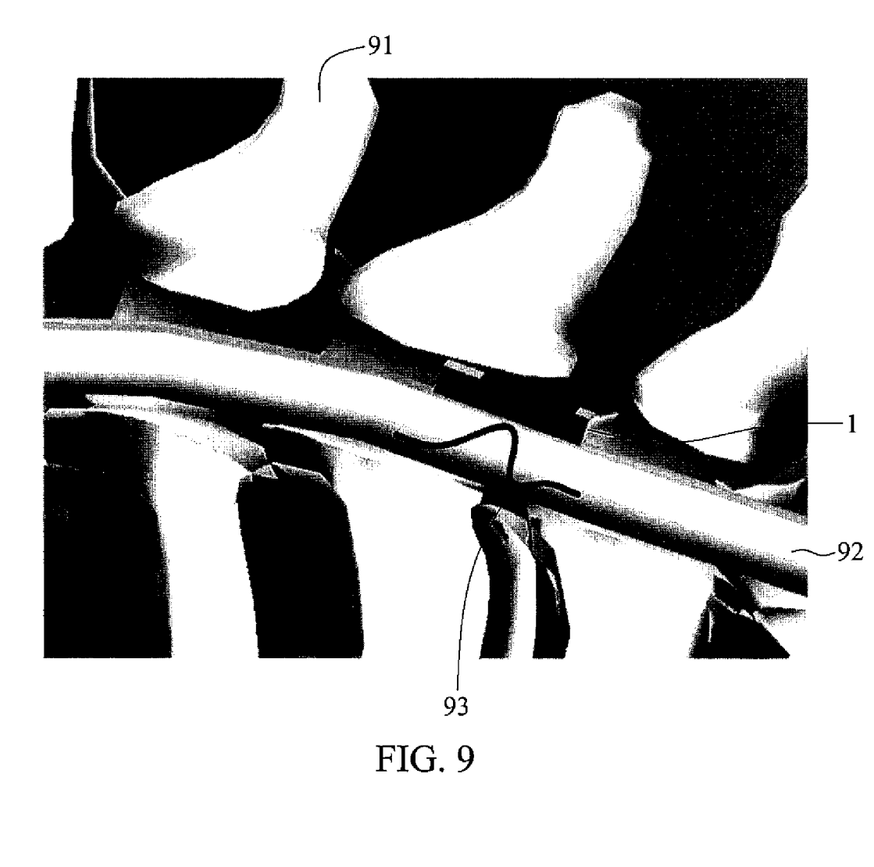
FIG. 9 is a schematic diagram showing placement of the nerve impulse signal stimulation device on spinal nerves of a human body.

FIG. 9 is a schematic diagram showing placement of the nerve impulse signal stimulation device 1 on spinal nerves of a human body. Referring to FIG. 9, there is a long narrow gap between the spine 91 and the spinal nerves 92. Therefore, the nerve impulse signal stimulation device 1 according to the present invention can be easily placed in the gap between the spine 91 and the spinal nerves 92 so as to induce a signal 93 in the spinal nerves 92, thereby helping the doctor to avoid damage to the spinal nerves 92 during an operation and improve the safety of the operation.

According to the present invention, a plurality of openings are formed to cause the nerve impulse signal stimulation device to obtain a parallel circuit structure, thereby increasing the current load and the magnetic field intensity, reducing the size of the device, and ensuring the safety of operations.

The above-described descriptions of the detailed embodiments are only to illustrate the preferred implementation according to the present invention, and it is not to limit the scope of the present invention. Accordingly, all modifications and variations completed by those with ordinary skill in the art should fall within the scope of present invention defined by the appended claims.

What is claimed is:

1. A method for fabricating a nerve impulse signal stimulation device, comprising:
   providing a substrate having a first surface and a second surface opposite to the first surface;
   forming a first metal layer on the first surface of the substrate;
   forming a second metal layer on the first metal layer;
   forming on the second metal layer a patterned resist layer that covers the second metal layer under the patterned resist layer;
   continuing formation of the second metal layer on a portion of the second metal layer that is not covered by the patterned resist layer;
   removing the patterned resist layer and the first metal layer and the second metal layer that are under the patterned resist layer so as to form a plurality of openings that expose a portion of the first surface of the substrate, a portion of the first metal layer and a portion of the second metal layer, wherein the second metal layer is divided by the openings into a plurality of strip-shaped structures having their ends electrically connected; and
   attaching a ferromagnetic material to the second surface of the substrate.

2. The method of claim 1, wherein each of the openings has a rib shape, and the openings are arranged in parallel to one another.

3. The method of claim 1, wherein the first metal layer is made of titanium.

4. The method of claim 1, wherein the second metal layer is made of copper.

5. The method of claim 1, further comprising, after removing the patterned resist layer and the first metal layer and the second metal layer that are under the patterned resist layer, forming a third metal layer on side surfaces of the first metal layer and upper and side surfaces of the second metal layer, and forming a fourth metal layer on upper and side surfaces of the third metal layer.

6. The method of claim 1, wherein the ferromagnetic material is made of cobalt, iron, bismanol, nickel, manganese antimonide, chromium oxide, manganese arsenide or manganese-zinc alloy.

7. A nerve impulse signal stimulation device, comprising:
a substrate having a first surface and a second surface opposite to the first surface;
a first metal layer formed on the first surface of the substrate;
a second metal layer formed on the first metal layer;
a plurality of openings exposing a portion of the first surface of the substrate, a portion of the first metal layer and a portion of the second metal layer, wherein the second metal layer is divided by the openings into a plurality of strip-shaped structures having their ends electrically connected; and
a ferromagnetic material attached to the second surface of the substrate.

8. The nerve impulse signal stimulation device of claim 7, wherein each of the openings has a rib shape, and the openings are arranged in parallel to one another.

9. The nerve impulse signal stimulation device of claim 7, wherein the first metal layer is made of titanium.

10. The nerve impulse signal stimulation device of claim 7, wherein the second metal layer is made of copper.

11. The nerve impulse signal stimulation device of claim 7, further comprising a third metal layer formed on side surfaces of the first metal layer and upper and side surfaces of the second metal layer, and a fourth metal layer formed on upper and side surfaces of the third metal layer.

12. The nerve impulse signal stimulation device of claim 7, wherein the ferromagnetic material is made of cobalt, iron, bismanol, nickel, manganese antimonide, chromium oxide, manganese arsenide or manganese-zinc alloy.

* * * * *